(12) United States Patent
Naito et al.

(10) Patent No.: US 7,504,012 B2
(45) Date of Patent: Mar. 17, 2009

(54) QUICKLY ACTIVATABLE STRUCTURE OF GAS SENSOR ELEMENT

(75) Inventors: Susumu Naito, Kariya (JP); Makoto Nakae, Nagoya (JP); Shinichiro Imamura, Chiryu (JP)

(73) Assignee: Denso Corporation, Kariya (JP)

( * ) Notice: Subject to any disclaimer, the term of this patent is extended or adjusted under 35 U.S.C. 154(b) by 698 days.

(21) Appl. No.: 10/831,129

(22) Filed: Apr. 26, 2004

(65) Prior Publication Data

US 2004/0217002 A1 Nov. 4, 2004

(30) Foreign Application Priority Data

May 1, 2003 (JP) ............... 2003-126559

(51) Int. Cl.
*G01N 27/41* (2006.01)
(52) U.S. Cl. ..................... 204/427; 73/23.32
(58) Field of Classification Search ......... 204/424–429; 205/781, 783.5–785; 73/23.31, 23.32
See application file for complete search history.

(56) References Cited

U.S. PATENT DOCUMENTS

| | | | | |
|---|---|---|---|---|
| 4,724,061 A | * | 2/1988 | Nyberg | ........ 204/412 |
| 5,288,389 A | * | 2/1994 | Yamada et al. | ........ 204/425 |
| 6,071,393 A | * | 6/2000 | Oshima et al. | ........ 204/425 |
| 6,258,232 B1 | * | 7/2001 | Hasegawa et al. | ........ 204/424 |
| 6,340,419 B1 | | 1/2002 | Nakae et al. | |
| 2002/0050455 A1 | * | 5/2002 | Kurokawa et al. | ........ 204/431 |
| 2003/0062904 A1 | * | 4/2003 | Katafuchi et al. | ........ 324/439 |

FOREIGN PATENT DOCUMENTS

| | | |
|---|---|---|
| JP | 02-062955 | 3/1990 |
| JP | 2000-206082 | 7/2000 |
| JP | 2002-141160 | 5/2002 |
| JP | 2003-090820 | 3/2003 |

OTHER PUBLICATIONS

Japanese Official Action dated Apr. 30, 2008, issued in corresponding Japanese Application No. 2003-126559, with English translation.

* cited by examiner

*Primary Examiner*—Kaj K Olsen
(74) *Attorney, Agent, or Firm*—Nixon & Vanderhye PC

(57) ABSTRACT

A gas sensor element which may be employed in measuring the concentration of gas such $O_2$ is provided. The gas sensor element is of a laminated type and designed to introduce gas to be measured into a measurement gas chamber through a diffusion resistor. The measurement gas chamber has a volume of 0.15 mm$^3$ in order to facilitate expelling of the gas remaining within the measurement gas chamber during transition of thermal activation of the gas sensor element.

3 Claims, 11 Drawing Sheets

DIRECTION OF
LAMINATION

QUICKLY ACTIVATABLE STRUCTURE OF GAS SENSOR ELEMENT

BACKGROUND OF THE INVENTION

1. Technical Field of the Invention

The present invention relates generally to an improved structure of a gas sensor element which is quickly activatable without sacrificing output characteristics thereof which may be built in a gas sensor employed in combustion control for automotive internal combustion engines.

2. Background Art

There are known exhaust emission feedback control systems which have an air-fuel ratio (A/F) sensor installed in an exhaust pipe of an automotive engine to measure the concentration of oxygen ($O_2$) contained in exhaust emissions and determine an air-fuel ratio in the engine as a function of the measured value for controlling combustion of the engine.

Particularly, when a three-way catalyst is used to convert air pollutants contained in exhaust emissions of automotive engines into harmless products, it is essential to control combustion of the engine so as to keep an air-fuel ratio of a mixture supplied to each combustion chamber of the engine within a limited range.

Such air-fuel ratio control typically employs an A/F sensor which is equipped with a laminated gas sensor element having a measurement gas chamber into which exhaust gasses are introduced through a diffusion resistor from outside the gas sensor element, a measurement gas electrode which is affixed to an oxygen ion-conductive solid electrolyte plate and exposed to the measurement gas chamber, and a reference gas electrode which is affixed to the solid electrolyte plate and exposed to a reference gas. The solid electrolyte plate, the measurement gas electrode, and the reference gas electrode constitute an electrochemical cell which works as a sensor cell to measure the concentration of oxygen within the measurement gas chamber.

For example, U.S. Pat. No. 6,340,419 B2, assigned to the same assignee as that of this application teaches an A/F sensor of the type as described above, the disclosure of which is totally incorporated therein by reference.

In recent years, there has been an increasing need for a gas sensor element of the A/F sensors used in the exhaust emission feedback control systems to have the ability to be activated quickly and high measurement accuracy.

Particularly, the quick activation of the A/F sensor element is one of objects of the exhaust gas regulations and is essential to reduce a large amount of hydrocarbon (HC) emitted greatly at cold start-up of engines.

The quick activation of the A/F sensor element requires a reduced heat capacity of the A/F sensor itself, that is, a reduction in size of the A/F sensor element and an increase in quantity of thermal energy produced to heat the A/F sensor element for activation thereof.

A rapid rise in temperature of the A/F sensor element for activation thereof, however, may lead to various concerns about output characteristics of the A/F sensor element.

The A/F sensor element of the above type is typically equipped with a diffusion resistor and designed to produce as a sensor output a limiting current in a one-cell type or a pump current in a two-cell type. Specifically, exhaust gasses are introduced through the diffusion resistor into a measurement gas chamber formed in a body of the A/F sensor element and then interact with a measurement gas electrode installed in the measurement gas chamber to produce the sensor output.

It is essential to heat the A/F sensor element up to a given activation temperature for producing the sensor output correctly. In the following discussion, a period of time until the A/F sensor element is activated sufficiently will also be referred to as an active transition period below.

During the active transition period, the gas staying in the measurement gas chamber of the A/F sensor element is heated rapidly so that it expands, but however, expelling of the gas from the measurement gas chamber is disturbed greatly by the diffusion resistor. This will result in a difficulty in introducing exhaust gasses into the measurement gas chamber when the A/F sensor element has reached the activation temperature, which leads to an error in determining an A/F ratio in the engine using the sensor output.

FIG. 14 demonstrates a time-sequential change in output of the A/F sensor element which was measured in the atmosphere where a A/F ratio is 18 (i.e., $N_2/O_2=4\%$).

A heater installed in the A/F sensor element was turned on to heat a body of the A/F sensor at a time 0. When the temperature of the A/F sensor element was low, it produced no sensor output. Upon a rise in temperature of the A/F sensor element, it started to produce the sensor output. After the A/F sensor element was warmed up completely, the sensor output should be kept constant, as indicated by a broken line, but actually varied, as indicated by a solid line.

In a case where the A/F sensor element is installed in an exhaust pipe of the engine, when the engine is at rest, that is, when the A/F sensor element is in an inactive state at an ambient temperature, the air entering from outside the exhaust pipe would exist around the A/F sensor element, so that the gas staying in the measurement gas chamber has substantially the same concentration of oxygen as that of the air. This often causes an output of the A/F sensor element such as the one, as indicated in FIG. 14, to indicate, in error, an A/F ratio leaner than that in the engine.

When the A/F sensor element has been activated, and the rise in temperature of the A/F sensor element has been stopped, the gas staying in the measurement gas chamber stops expanding and is replaced with gas flowing outside the A/F sensor element by a pumping operation of the A/F sensor element, so that the sensor output is kept constant, as illustrated in FIG. 14.

Specifically, the output error of the A/F sensor element will result in a delay in producing a correct sensor output, which is objectionable to the quick activation of the A/F sensor element.

There has been proposed the following measures to alleviate the above problem.

Rapid expelling of the gas staying in the measurement gas chamber is achieved by decreasing the degree of diffusion resistance of the diffusion resistor. This, however, results in a difficulty in producing a limiting current as well as a decrease in the output error of the A/F sensor element, thus decreasing the measurement accuracy of the A/F sensor element.

Usually, an exhaust gas emitted from automotive engines is subjected to a great change during operation of the engine. When the pressure of gas to be measured by the A/F sensor element varies, the decreased diffusion resistance may also result in instability (i.e., pulsation) of the sensor output arising from the variation in the gas.

The output error is eliminated by decreasing a rate at which the A/F sensor element is heated up so as to permit the gas to be discharged from the measurement gas chamber completely before the temperature of the A/F sensor element reaches a activation temperature thereof. This, however, results in a difficulty in activating the A/F sensor element quickly.

The above problems are also encountered by another type of gas sensors which are designed to introduce a gas to be measured into the measurement gas chamber through the diffusion resistor and required both to be activated quickly and to have high measurement accuracy.

SUMMARY OF THE INVENTION

It is therefore a principal object of the present invention to avoid the disadvantages of the prior art.

It is another object of the present invention to provide an improved structure of a laminated gas sensor element capable of being activated quickly and minimizing an output error during a transition of activation thereof.

According to one aspect of the invention, there is provided a laminated gas sensor element which may be built in a gas sensor for measuring the concentration of gas such as $O_2$ used in an air-fuel ratio control system of automotive vehicles. The gas sensor element comprises: (a) a diffusion resistor; (b) a measurement gas chamber into which a gas to be measured is introduced through the diffusion resistor; (c) an oxygen ion conductive solid electrolyte member; (d) a measurement gas electrode affixed to the solid electrolyte member, the measurement gas electrode being exposed to the gas within the measurement gas chamber; and (e) a reference gas electrode affixed to the solid electrolyte member. The reference gas electrode is exposed to a reference gas and works as an electrochemical cell together with the measurement gas electrode. The measurement gas chamber has a volume of 0.15 $mm^3$ or less.

An output error of a gas sensor element of the above type arises, as discussed in the introductory part of this application from the fact that expansion of gas staying in the measurement gas chamber by rapid heating of the gas sensor element is disturbed by the diffusion resistor during a transition of activation of the sensor element, thereby resulting in a difficulty in entrance of gas from outside the gas sensor element into the measurement gas chamber. In order to avoid this, the gas sensor element of the invention is designed to have the measurement gas chamber whose volume is 0.15 $mm^3$ or less, thereby decreasing the amount of the gas staying within the measurement gas chamber without sacrificing the ability of the diffusion resistor. Specifically, the gas sensor element is capable of expelling the gas outside the measurement gas chamber before completion of activation of the gas sensor element, thereby permitting the gas sensor element to be activated quickly and minimizing an output error during a transition of the activation.

The invention may be used with all laminated gas sensor element of the type in which gas to be measured is introduced into a measurement gas chamber through a diffusion resistor.

In the preferred mode of the invention, the measurement gas electrode works as a pumping electrode which pumps oxygen contained in the gas into or out of the measurement gas chamber. The pumping electrode has an area Sp exposed to the measurement gas chamber which meets a condition of Vc/Sp<0.02 mm where Vc is the volume of the measurement gas chamber.

The measurement gas chamber has a height of 5 to 18 μm in a thickness-wise direction of the gas sensor element.

The measurement gas chamber may alternatively have a height of 10 to 15 μm in the thickness-wise direction of the gas sensor element.

The gas sensor element may further comprise a heater which heats the gas sensor element up to a temperature required to activate the gas sensor element. The heater works to increase a temperature of the gas sensor element at a rate of 100 to 250° C./sec.

The electrochemical cell works as a pump cell. The gas sensor element may further comprise an electrochemical cell serving as a sensor cell. The sensor cell includes a sensor cell electrode which is affixed to said solid electrolyte member and exposed to said measurement gas chamber. The sensor cell works to produce an electrical signal indicative of a difference in concentration between a specified component of the gas in said measurement gas chamber and the specified component of the reference gas. The electrical signal is used to control an operation of the pump cell.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
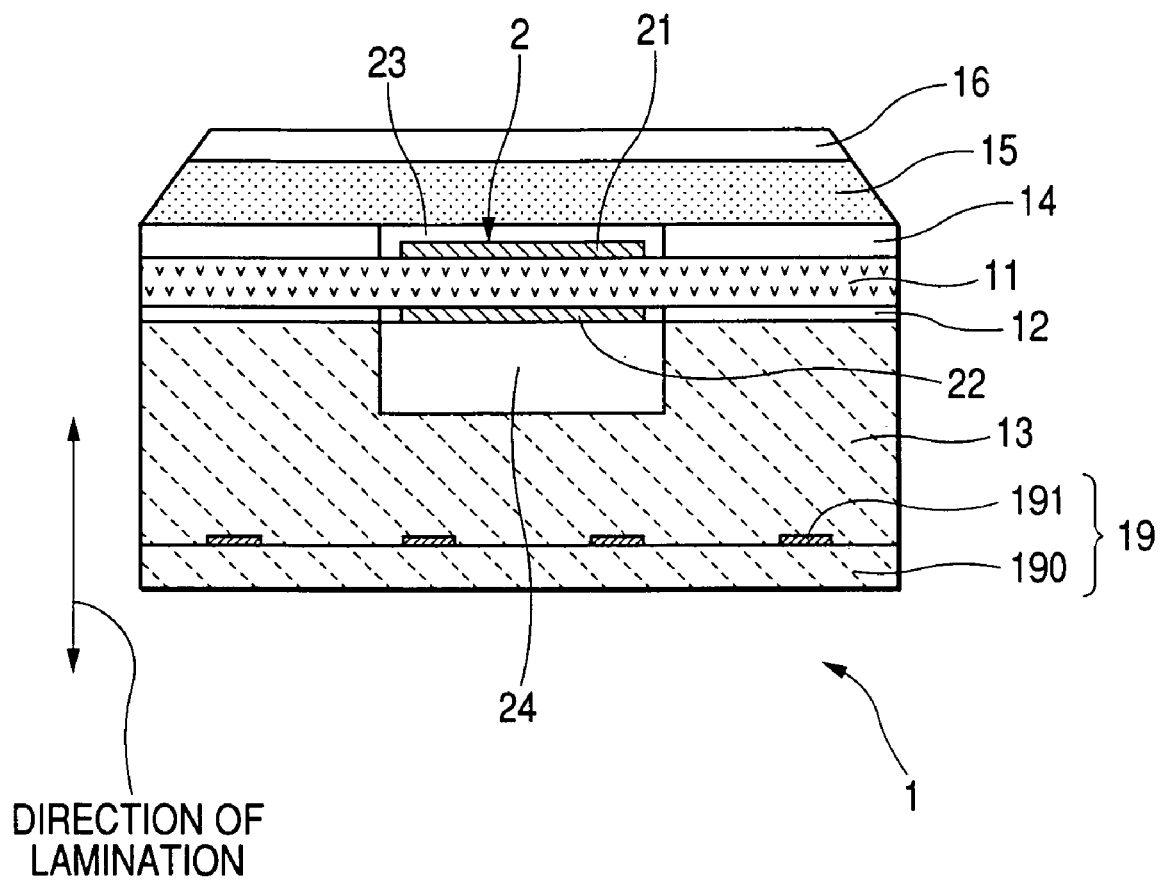
FIG. 1 is a transverse sectional view which shows a gas sensor element according to the first embodiment of the invention.
Figure 2:
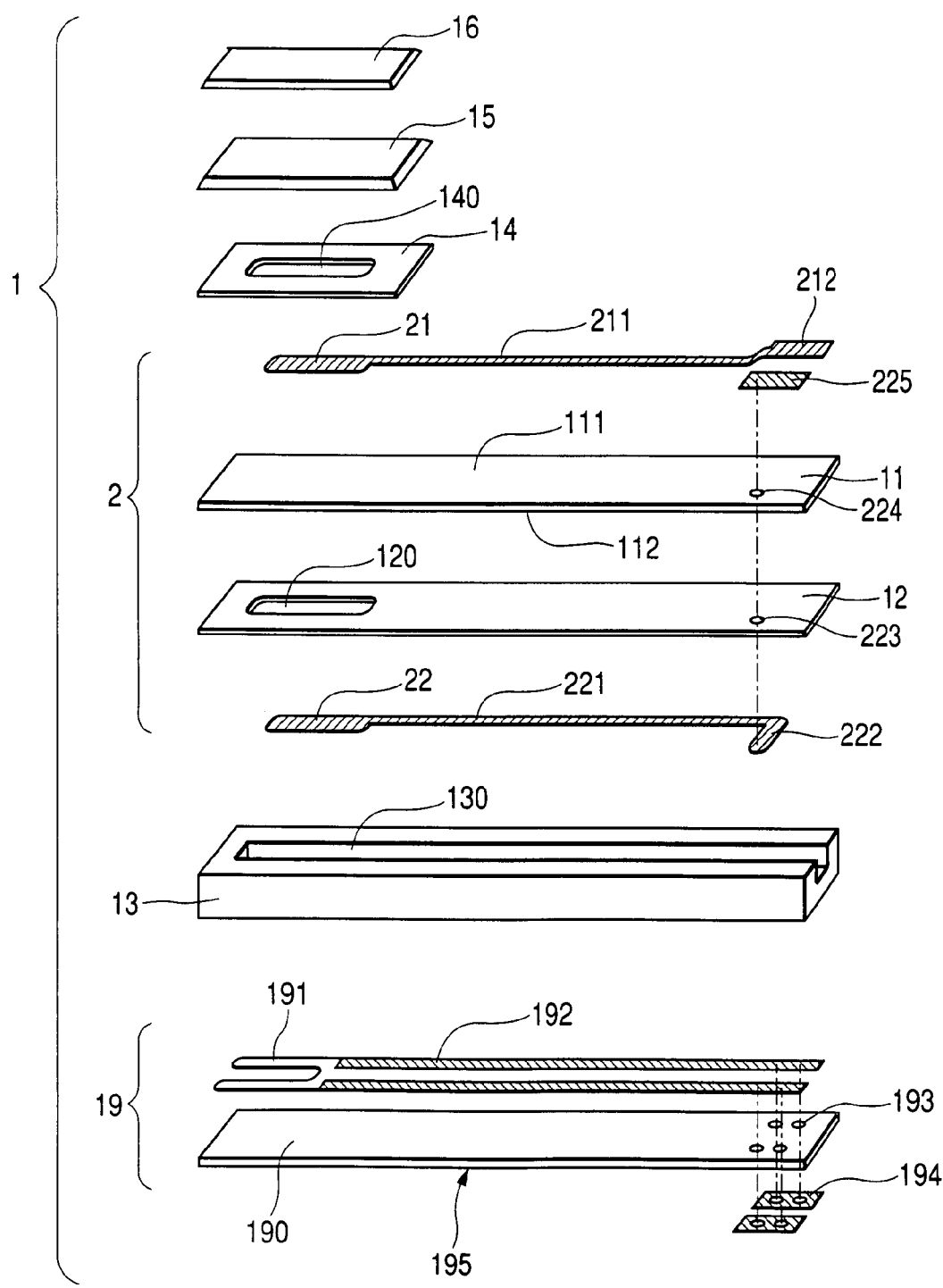
FIG. 2 is an exploded view which shows the gas sensor element of FIG. 1.
Figure 3:
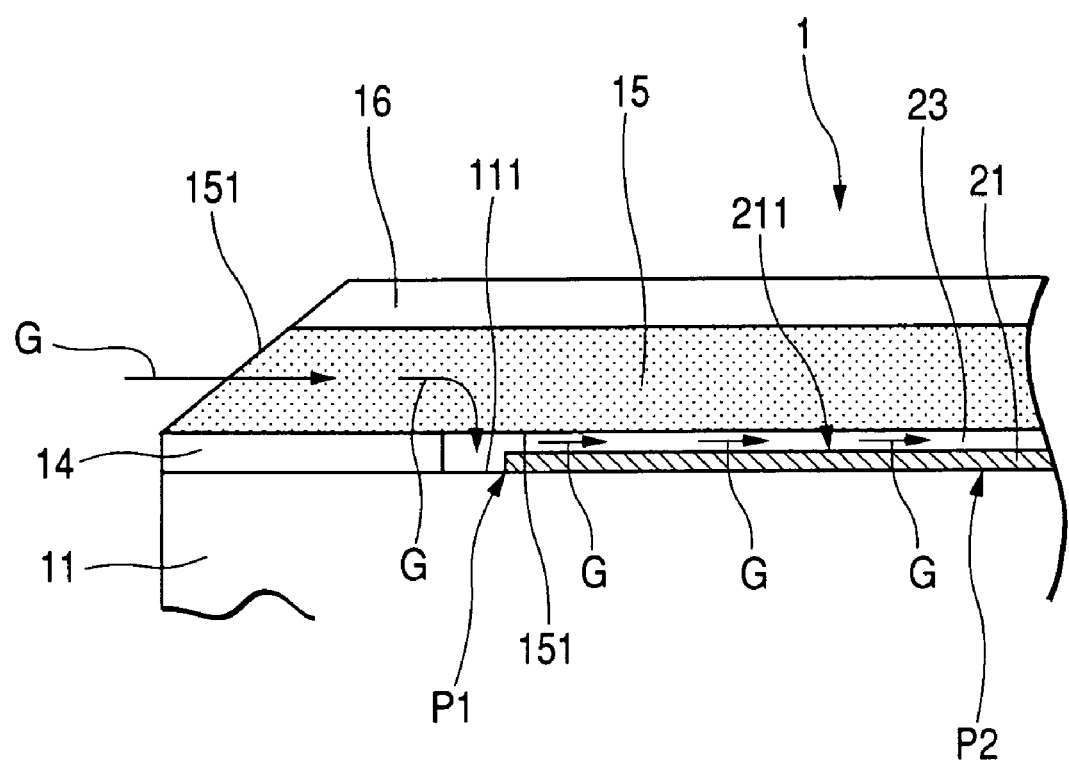
FIG. 3 is a partially sectional view which shows a flow of gas into the gas sensor element of FIG. 1.

Referring now to the drawings, wherein like numbers refer to like parts in several views, particularly to FIGS. 1, 2 and 3, there is shown a gas sensor element 1 according to the first embodiment of the invention. The gas sensor element 1 is to be incorporated within a body of a gas sensor which may be installed in an exhaust pipe of an automotive engine to measure the concentration of oxygen ($O_2$) contained in exhaust gasses of the engine in order to determine an air-fuel (A/F) ratio of a mixture supplied to combustion chambers of the engine for use in an exhaust emission feedback control system for controlling the combustion of the engine. An overall structure of such a gas sensor is not essential for this invention, and explanation thereof in detail will be omitted here.

The gas sensor element 1 is made of a laminate of a heater 19, a spacer 13, an insulating layer 12, an oxygen ion-conductive solid electrolyte layer 11, a spacer 14, a diffusion resistance layer 15, and a dense layer 16.

The gas sensor element 1 also includes a measurement gas electrode 21 and a reference gas electrode 22 which are affixed to opposed surfaces of the solid electrolyte layer 11 to form an electrochemical cell 2. The spacer 13 has a reference gas chamber 24 defined therein along with the insulating layer 12 into which a reference gas such as air is introduced. The spacer 14 has a measurement gas chamber 23 along with the solid electrolyte layer 11 and the diffusion resistance layer 15 into which exhaust gasses (will also referred to as a measurement gas below) of the engine to be measured enter. The volume Vc of the measurement gas chamber 23 is, as will be described later in detail, 0.15 $mm^3$ or less. The reference gas electrode 22 is exposed to the reference gas chamber 24. The measurement gas electrode 21 is exposed to the measurement gas chamber 23.

The heater 19 is, as clearly shown in FIG. 2, made up of a heater substrate 190, a heater element 191, and a pair of leads 192. The heater element 191 and the leads 192 are affixed to a surface of the heater substrate 190. The leads 192 are electrically connected through conductive material-coated holes 193 formed in the heater substrate 190 to terminals 194 affixed to the underside of the heater substrate 190. The terminals 194 are electrically connected to a power supply (not shown) to supply power to the heater element 191 to heat the gas sensor element 1 up to a given activation temperature thereof required to activate the operation of the gas sensor element 1 correctly.

The spacer 13 has formed therein a groove 130 extending longitudinally to define the reference gas chamber 24.

The insulating layer 12 has formed therein an opening or window 120 through which the reference gas electrode 22 is exposed to the reference gas chamber 24.

The solid electrolyte layer 11 has the surface 111 to which the measurement gas electrode 21, a lead 211, and a terminal 212 are affixed. The terminal 212 is exposed outside the gas sensor element 1. The solid electrolyte layer 11 also has the surface 112 covered with the insulating layer 12. The reference gas electrode 22 is affixed to the surface 112 through the window 120 of the insulating layer 12 and connected electrically to an internal terminal 222 through a lead 221. The internal terminal 222 and the lead 221 are affixed to a surface of the insulating layer 12. The reference gas electrode 22 is connected electrically to a terminal 225 affixed to the solid electrolyte layer 11 through conductive material-coated holes 223 and 224 formed in the insulating layer 12 and the solid electrolyte layer 11.

The measurement gas electrode 21, the solid electrolyte layer 11, and the reference gas electrode 22 constitute the electrochemical cell 2.

The spacer 14 affixed to the surface 111 of the solid electrolyte layer 11 has formed therein a window 140 to which the measurement gas electrode 21 is exposed. The spacer 14 is substantially identical in width with the solid electrolyte layer 11 and has a length slightly longer than that of the measurement gas electrode 21.

The diffusion resistance layer 15 is made of a porous material and affixed to the spacer 14 to close the window 140. The dense layer 16 is a gas-impermeable material and affixed to an upper surface of the diffusion resistance layer 15. Instead of the diffusion resistance layer 15, a pinhole may be formed in the dense layer 16 as a diffusion resistor working to minimize diffusion of gas entering the gas sensor element 1. The pinhole may also be filled with a porous material. Instead of the pinhole, a gas inlet path partially filled with a porous material may be formed which communicates with the measurement gas chamber 23.

The gas sensor element 1 designed to introduce gas into the measurement gas chamber 23 through such a diffusion resistor works to produce a limiting current as a function of the concentration of oxygen contained in the gas. Specifically, in the absence of the diffusion resistor, the current flowing between the electrodes 21 and 22 increases with an increase in voltage applied thereto. In the presence of the diffusion resistor, flat ranges within which the current is kept constant regardless of an increase in voltage applied across the electrodes 21 and 22 appear within specified voltage ranges. The current (i.e., the limiting current) within each of the flat ranges represents the concentration of oxygen within the measurement gas chamber 23.

The heater substrate 190, the spacer 13, the insulating layer 12, the spacer 14, and the dense layer 16 are all made of a gas-impermeable dense alumina ceramic. The solid electrolyte layer 11 is made of a partially stabilized zirconia. The diffusion resistance layer 15 is made of a gas-permeable porous alumina ceramic.

The parts other than the solid electrolyte layer 11 may be made of ceramic material such as zirconia in order to avoid shrinkage created in a firing process when the gas sensor element 1 is produced.

The measurement gas chamber 23 is, as described above, surrounded by the solid electrolyte layer 11, the spacer 14, and the diffusion resistance layer 15.

The diffusion resistance layer 15, as clearly shown in FIG. 3, has a side surface 151 not covered with the dense layer 16. The measurement gas, as indicated by arrows G, enters the side surface 151. When the measurement gas remaining within the measurement gas chamber 23 expands during transition of activation of the gas sensor element 1 (i.e., the electrochemical cell 2), it passes through the diffusion resistance layer 15 and escapes outside the gas sensor element 1 from the side surface 151.

The volume Vc of the measurement gas chamber 23 is 0.13 $mm^3$ and may be measured three-dimensionally using an X-ray CT scanner. The volume Vc, as referred to herein, is a net volume of the measurement gas chamber 23 not including the measurement gas electrode 21. For example, in a case where a pinhole is formed in the dense layer 16 instead of the diffusion resistance layer 15, the volume Vc excludes the volume of the pinhole.

The electrochemical cell 2 serves as a pump cell working to pump oxygen ($O_2$) out of or into the measurement gas chamber 23 upon application of voltage to the measurement gas electrode 21 and the reference gas electrode 22. For example, when the voltage is applied across the measurement gas electrode 21 and the reference gas electrode 22 so that a higher potential may appear at the measurement gas electrode 21, the reference gas electrode which is at a lower potential works to decompose or ionize oxygen molecules to produce oxygen ions which, in turn, travel to the measurement gas electrode 21 and are reduced thereby to oxygen molecules. This operation is generally referred to as oxygen-pumping.

The measurement gas electrode 21 has a pumping portion contributing to the oxygen-pumping which has a maximum area Sp which is substantially in parallel to the solid electrolyte layer 11 and exposed to the measurement gas chamber 23. The area Sp is 7.5 mm$^2$ and meets a relation of Vc/Sp=0.017 mm.

The height h of the measurement gas chamber 23 in a direction of lamination (i.e., a thickness-wise direction) of the gas sensor element 1 that is, as shown in FIG. 3, the distance between a portion of the surface 111 of the solid electrolyte layer 11 exposed to the measurement gas chamber 23 and a portion of the surface 151 of the diffusion resistance layer 15 exposed to the measurement gas chamber 23 is 15 μm.

A failure in operation of the gas sensor element 1 resulting in an error of an output thereof usually arises from the fact that expansion of the gas remaining within the measurement gas chamber 23 due to rapid heating of the gas sensor element 1 during transition of activation thereof is disturbed by the diffusion resistance layer 15, thus increasing a difficulty in entrance of exhaust gasses into the measurement gas chamber 23 from outside the gas sensor element 1.

In order to avoid the above problem, the gas sensor element 1 is designed to have the volume Vc of the measurement gas chamber 23 that is 0.15 mm$^3$ or less to minimize the amount of gas staying within the measurement gas chamber 23 to complete expelling of the gas from the measurement gas chamber 23 before completion of activation of the gas sensor element 1. This minimizes the error of output of the gas sensor element 1 during the transition of activation of the gas sensor element 1 and allows the activation to be sped up.

The gas sensor element 1 of this embodiment is so structured as to discharge the gas in the measurement gas chamber 23 outside the gas sensor element 1 within five (5) seconds. Therefore, use of the gas sensor element 1 enables exhaust emission feedback control systems to be brought into a normally operable condition within about five (5) seconds after start-up of the engine. This permits the efficiency of emissions purification to be increased using a three-way catalytic converter immediately after the start-up of the engine to decrease the amount of HC emissions greatly.

Figure 4:
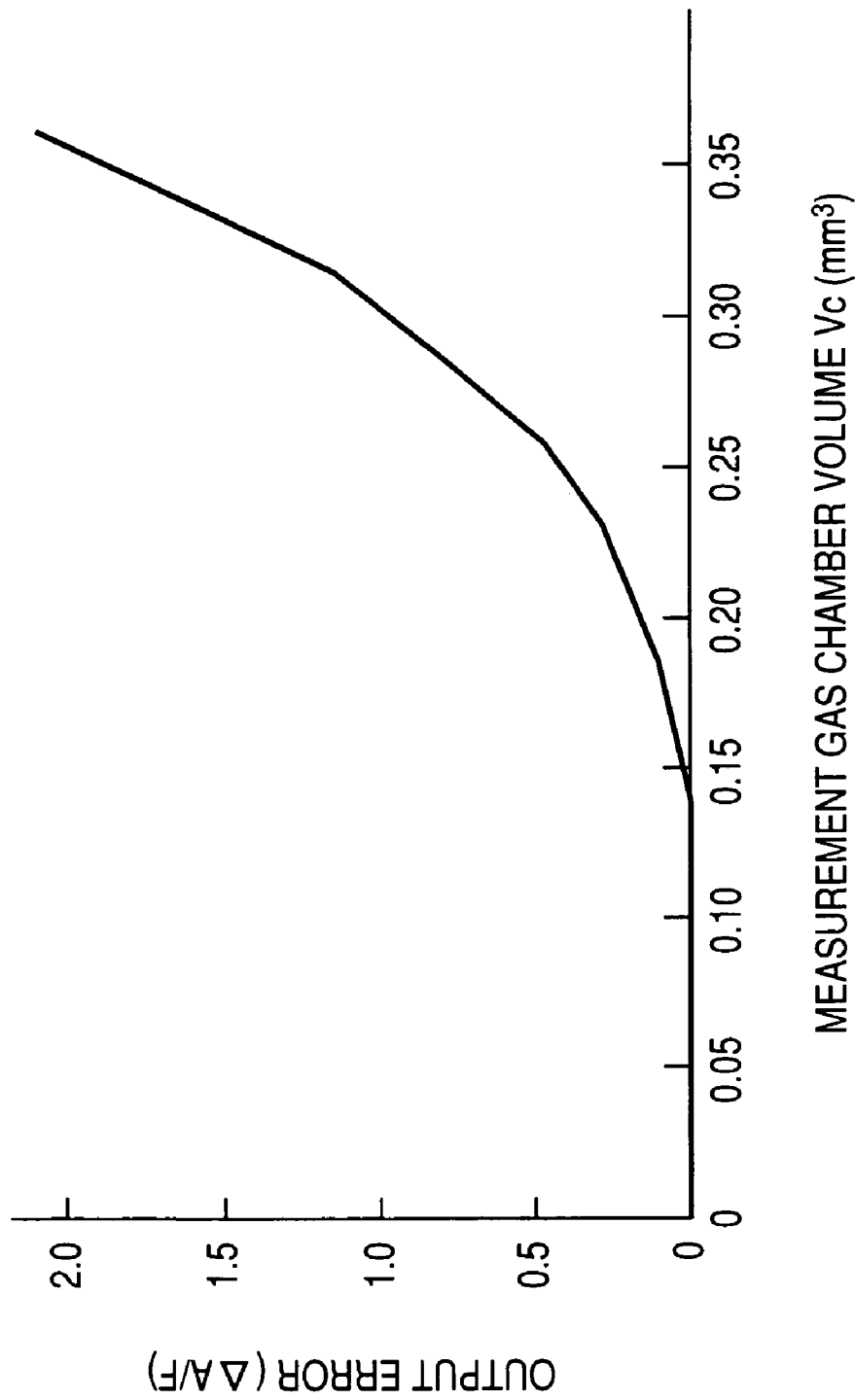
FIG. 4 is a graph which demonstrates an experimentally measured relation between the volume of a measurement gas chamber and an error of an output of the gas sensor element of FIG. 1 arising at cold start-up of an automotive engine.

FIG. 4 demonstrates an experimentally measured relation between the volume Vc of the measurement gas chamber 23 and an error of an output of the gas sensor element 1 arising at cold start-up of an automotive engine.

We prepared many test samples identical in structure with the gas sensor element 1 as described above. The test samples had the volumes Vc of the measurement gas chamber 23 over a range of 0 to 0.35 mm$^3$. Some of the test samples had a volume Vc of zero (0) in which the measurement gas electrode 21 occupies the whole of the window 140, and the measurement gas electrode 21 is in close contact with the diffusion resistance layer 15. The ordinate axis represents an output error that is a difference between a maximum output of each of the test samples when the test sample was placed in a nitrogen atmosphere containing 4% oxygen and heated to activate the test sample at five (5) seconds and an output thereof placed in a steady state after heated. The abscissa axis represents the volume Vc of the measurement gas chamber 23.

The graph shows that when the volume Vc is 0.15 mm$^3$ or less, the test samples hardly produce output errors and operate correctly.

Figure 5:
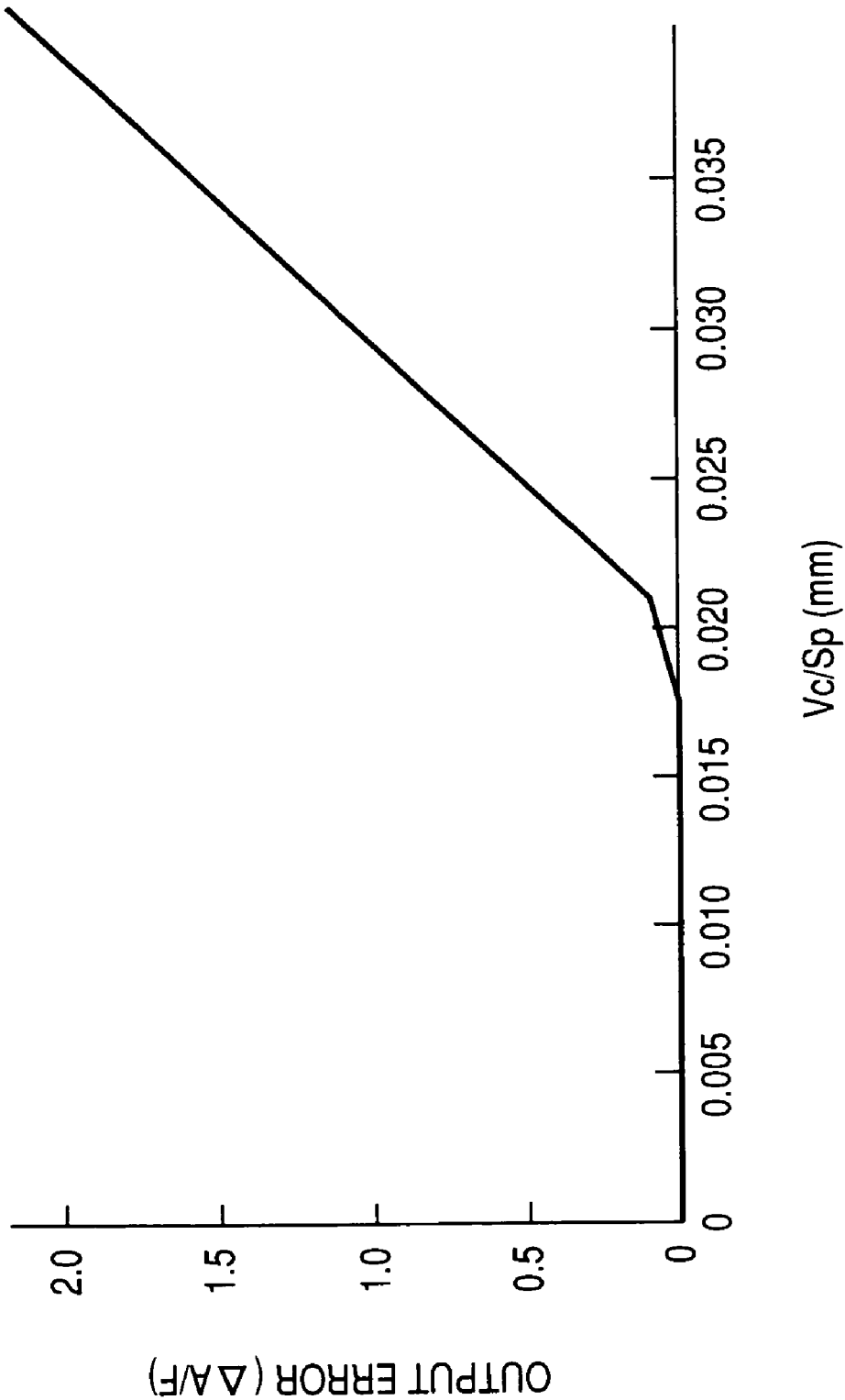
FIG. 5 is a graph which demonstrates an experimentally measured relation between an error of an output of the gas sensor element of FIG. 1 arising at cold start-up of an automotive engine and a ratio of the volume of a measurement gas chamber to an area of a measurement gas electrode exposed to the measurement gas chamber.

FIG. 5 demonstrates an experimentally measured relation between an error of an output of the gas sensor element 1 arising at cold start-up of an automotive engine and a ratio of the volume Vc of the measurement gas chamber 23 to an area Sp of the measurement gas electrode 21 exposed to the measurement gas chamber 23.

We prepared many test samples identical in structure with the gas sensor element 1. The test samples had Vc-Sp ratios over a range of 0 to 0.035 mm. Some of the test samples had the structure in which the spacer 14 is removed, and the measurement gas electrode 21 is in close contact with the diffusion resistance layer 15 and had a Vc-Sp ratio of zero (0). The ordinate axis represents the same output error as that in FIG. 4. The abscissa axis represents the Vc-Sp ratio.

The graph of FIG. 5 shows that when the Vc-Sp ratio (i.e., Vc/Sp) is 0.02 mm or less, the test samples hardly produce undesirable output errors impinging on an operation of the exhaust emission feedback control systems. When the Vc-Sp ratio is greater than 0.02 mm (i.e., Vc/Sp$\geqq$0.02 mm), it would result in a lack in expelling of the gas from the measurement gas chamber 23, thus consuming much time until the output error is converged or disappears. Note that in a case where the gas sensor element 1 is equipped with a plurality of pumping electrodes, the area Sp is a total area of the pumping electrodes exposed to the measurement gas chamber 23.

Figure 6:
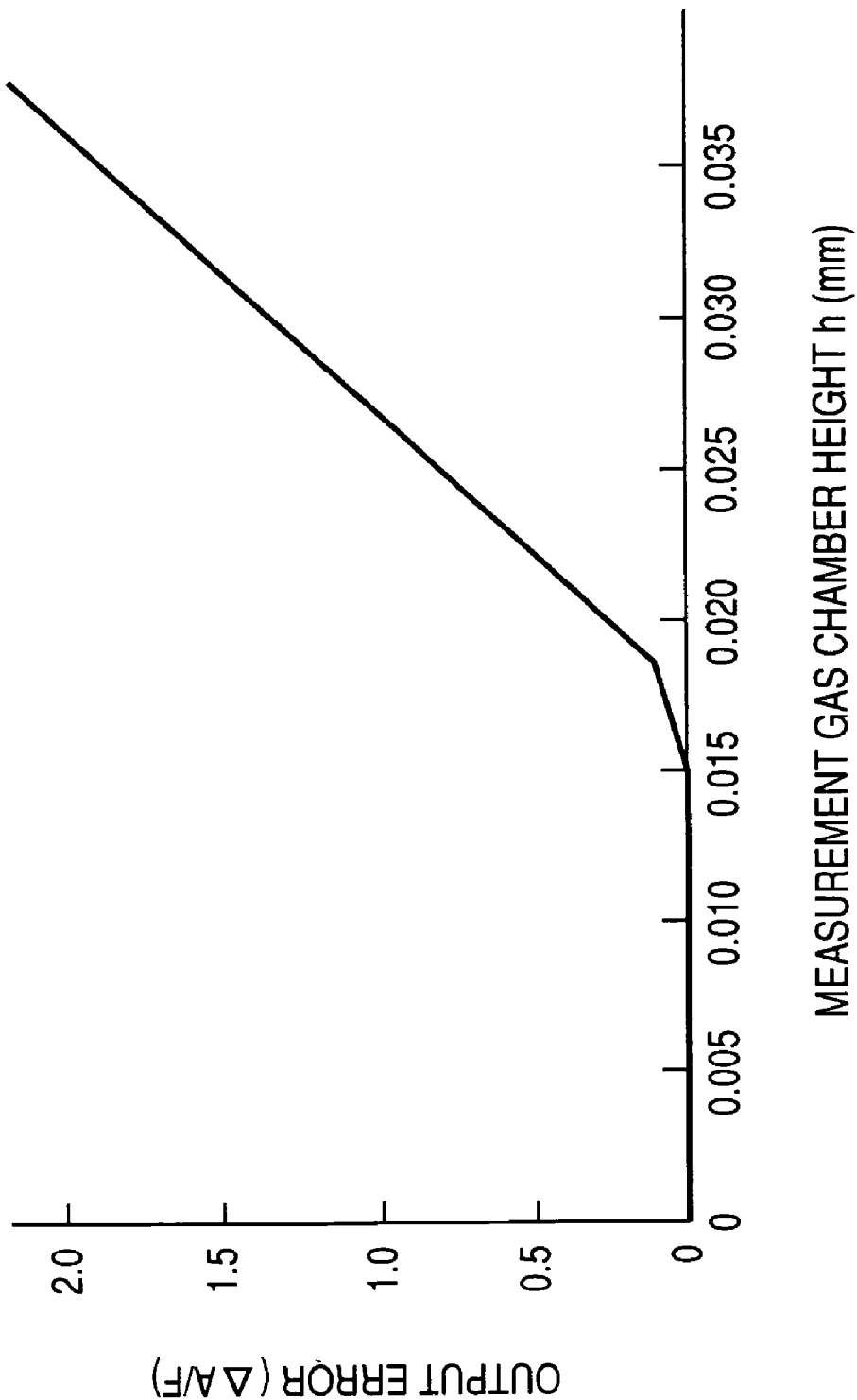
FIG. 6 is a graph which demonstrates an experimentally measured relation between an error of an output of the gas sensor element of FIG. 1 arising at cold start-up of an automotive engine and the height of a measurement gas chamber.
Figure 7:
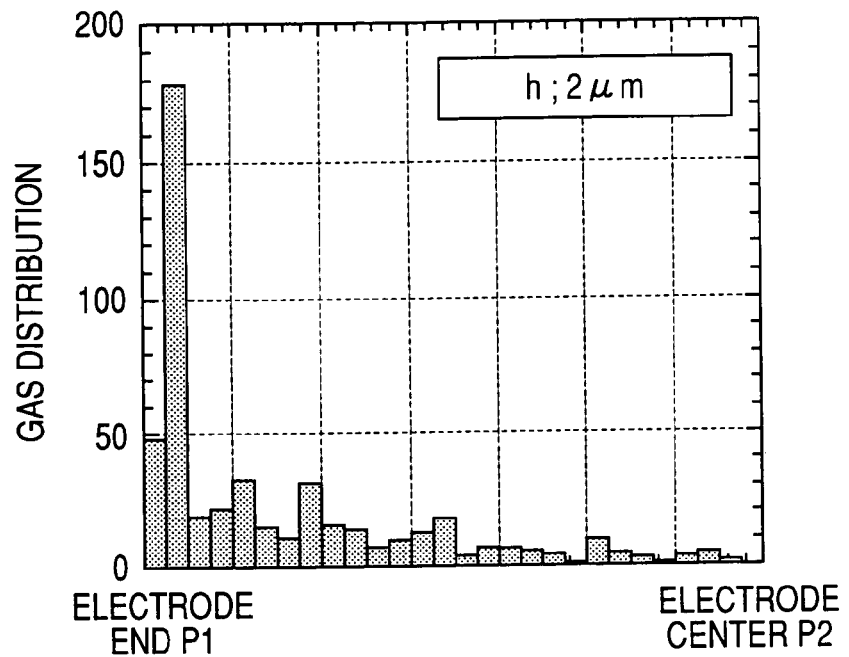
FIGS. 7, 8, 9, and 10 are graphs which demonstrate distributions of gas which has entered at a diffusion resistance layer and reached a measurement gas electrode 21 for heights h=2 μm, 5 μm, 10 μm, and 30 μm which were measured through Monte Carlo simulations.
Figure 8:
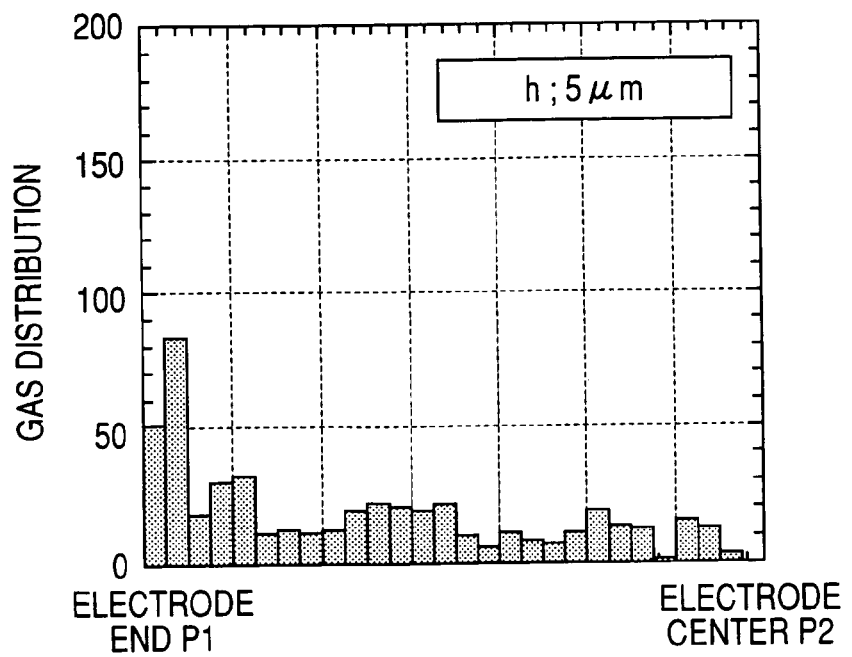
Figure 9:
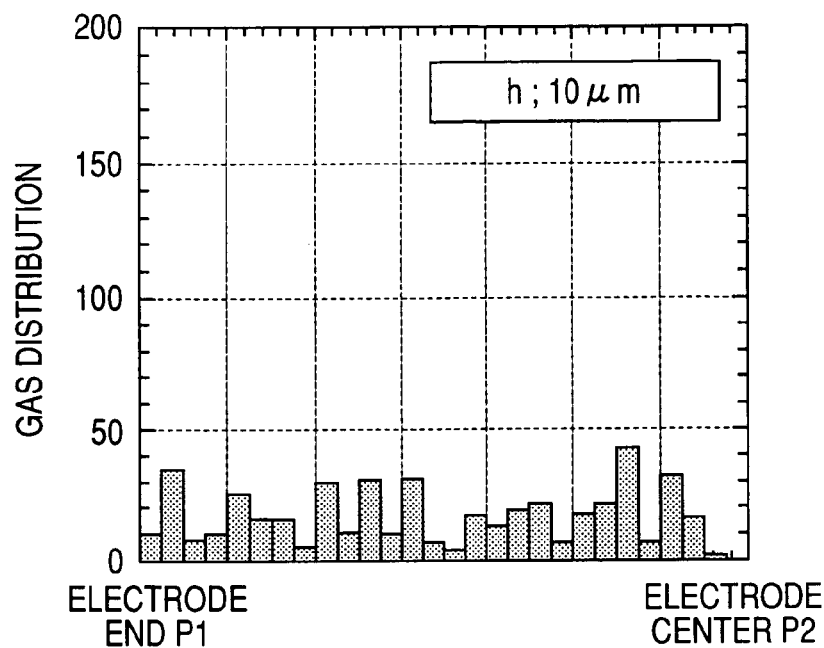
Figure 10:
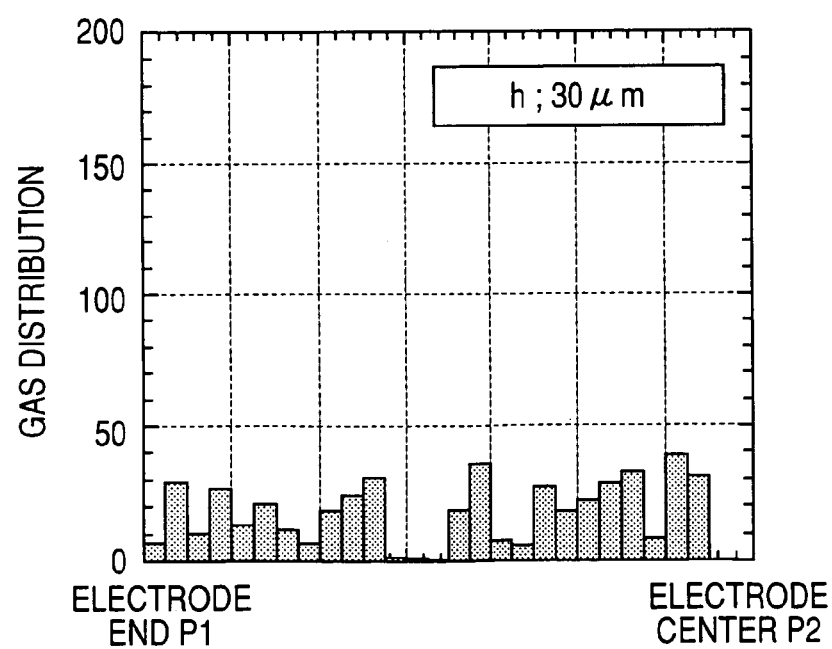

FIG. 6 demonstrates an experimentally measured relation between an error of an output of the gas sensor element 1 arising at cold start-up of an automotive engine and the height h of the measurement gas chamber 23, as described above.

We prepared many test samples identical in structure with the gas sensor element 1. The test samples had heights h over a range of 0 to 0.035 mm. Some of the test samples had the structure in which the spacer 14 is removed, and the measurement gas electrode 21 is in close contact with the diffusion resistance layer 15 and had a height h of zero (0). The ordinate axis represents the same output error as that in FIG. 4. The abscissa axis represents the height h.

The graph of FIG. 6 shows that when the height h 0.015 mm (i.e., 15 μm) or less, the test samples hardly produce undesirable output errors impinging on an operation of the exhaust emission feedback control systems.

FIGS. 7 to 10 demonstrate distributions of gas which has entered at the diffusion resistance layer 15 and reached the measurement gas electrode 21 for h=2 μm, 5 μm, 10 μm, and 30 μm which were measured through Monte Carlo simulations.

The simulations were performed by determining the behavior of gas particles between entrance thereof at the diffusion resistance layer 15 and a time when the gas has reached the measurement gas electrode 21 using the Monte Carlo method and finding the distribution of the gas over the measurement gas electrode 21. The distributions of gas in FIGS. 7 to 10 each range from, as shown in FIG. 3, the end P1 to the center P2 of the measurement gas electrode 21.

The Monte Carlo method is a technique which expresses the behavior of each of objects such as gas particles moving randomly using random numbers and obtains such phenomenon and distribution statistically. The simulations were made to determine a direction of Brownian motion of each of the gas particles after they collide with each other based on changes in direction of the motion of the gas particles using uniform random numbers.

The graphs of FIGS. 7 to 10 show that when the height h of the measurement gas chamber 23 is greater than 5 μm, it causes the measurement gas to reach the center P2 of the measurement gas electrode 21, and when the height h of the measurement gas chamber 23 is greater than 10 μm, it ensures substantially a uniform spread of most of the measurement gas from the end P1 to the center P2 of the measurement gas electrode 21. The graphs also show that when the height h of the measurement gas chamber 23 is smaller than 2 µm, it results in a lack of the amount of the measurement gas reaching the center P2 of the measurement gas electrode 21, that is, an increase in the amount of the measurement gas on the side of the end P1, thus leading to the instability of the limiting current produced by the electrochemical cell 2 (i.e., irregularity in ranges of the limiting current), which will result in decreased measurement accuracy of the gas sensor element 1, and that when the height h of the measurement gas chamber 23 is 30 µm, the volume Vc of the measurement gas chamber 23 may be too great to complement the beneficial effects of the invention.

From the above analysis, we have found that the height h is preferably between 5 πm and 18 µm, and more preferably between 10 µm and 15 µm.

Figure 11:
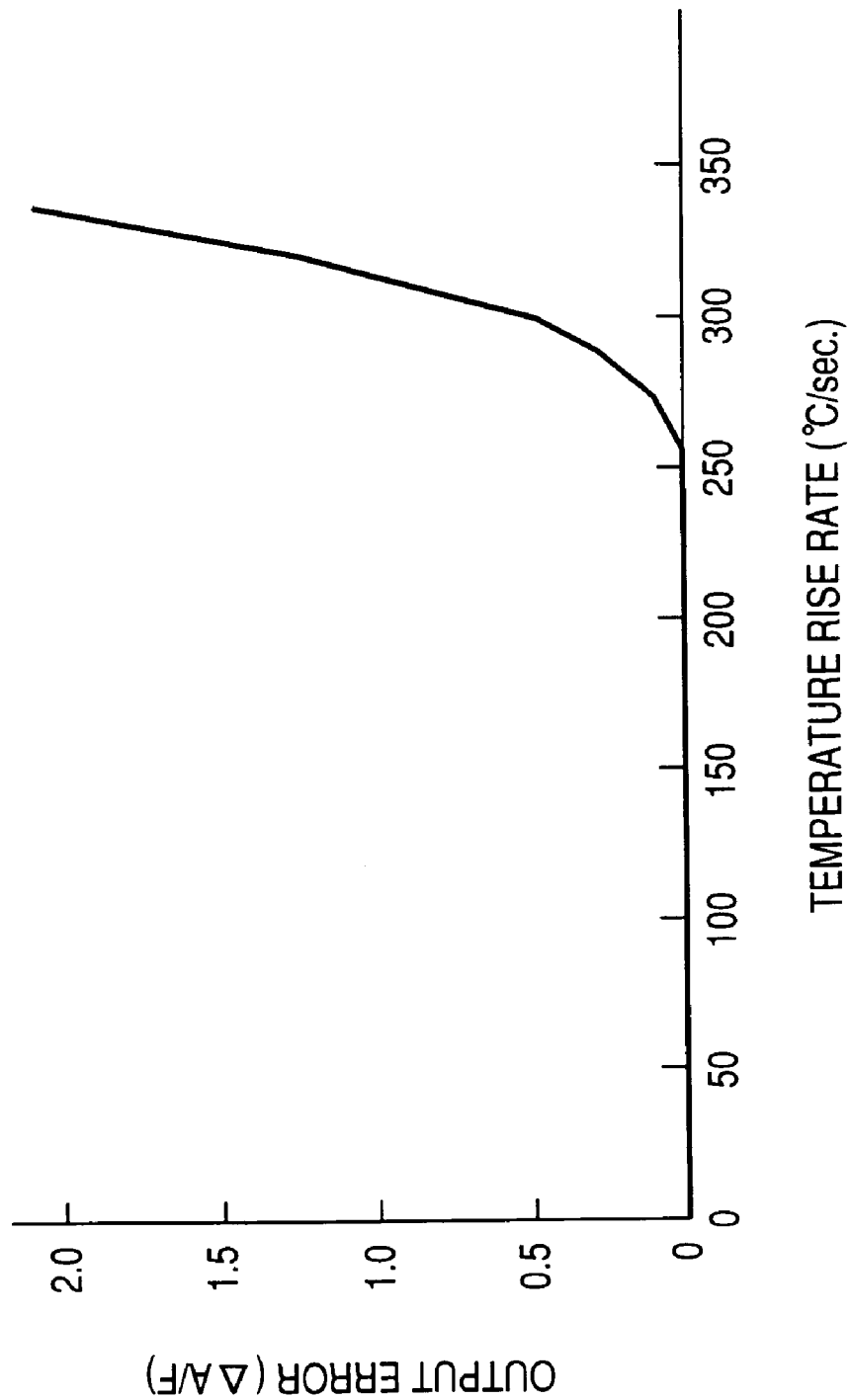
FIG. 11 is a graph which shows an experimentally measured relation between an error of an output of the gas sensor element of FIG. 1 arising at cold start-up of an automotive engine and a rise speed of temperature of the gas sensor element.

FIG. 11 demonstrates an experimentally measured relation between an error of an output of the gas sensor element 1 arising at cold start-up of an automotive engine and a rise speed of the temperature of the gas sensor element 1 (i.e., a rate at which the temperature of the gas sensor element 1 is increased).

We prepared many test samples identical in structure with the gas sensor element 1. Adjustment of the temperature of the gas sensor element 1 was achieved by increasing or decreasing the power supplied to the heater 19. A zero (0) temperature rise speed means that the heater 19 is at rest. The ordinate axis represents the same output error as that in FIG. 4. The abscissa axis represents the rise speed of the temperature of the gas sensor element 1.

The graph of FIG. 11 shows that when the rise speed is 250° C./sec. or less, the test samples produce no undesirable output errors. When the rise speed is less than 100° C./sec., it is difficult to ensure desired quick activation of the gas sensor element 1. When the rise speed is more than 250° C./sec., the temperature of the heater 19 may exceed an upper limit of thermal shock resistance of the gas sensor element 1. It is, thus, advisable that the rise speed of the temperature of the gas sensor element 1 be set to within a range of 100° C./sec. to 250° C./sec. This enables the temperature of the gas sensor element 1 to be elevated from a room temperature to a desired activation temperature within five (5) seconds. In a case where the gas sensor element 1 is installed in an exhaust pipe of an automotive engine and used in the exhaust emission feedback control system, as described above, heating of the gas sensor element 1 at a rise speed of 100° C./sec. to 250° C./sec. enables HC emissions to be controlled desirably immediately following a cold start-up of the engine, which meets recent severe emission regulations.

Figure 12:
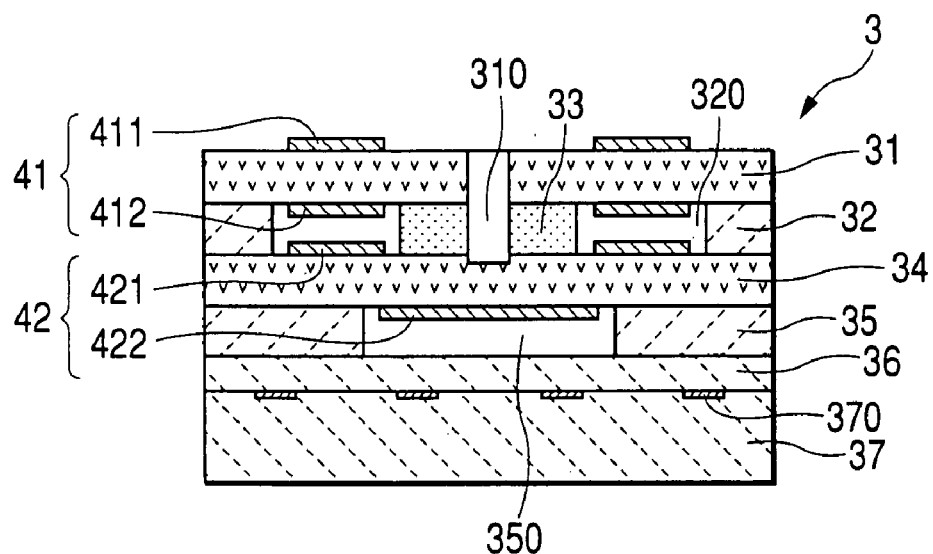
FIG. 12 is a transverse sectional view which shows a gas sensor element according to the second embodiment of the invention.

FIG. 12 shows a gas sensor element 3 according to the second embodiment of the invention which has a two-cell structure and made of a laminate of solid electrolyte layers 31 and 34, spacers 32 and 35, an insulating layer 36, and a heater substrate 37.

The gas sensor element 3 has a measurement gas chamber 320 surrounded by the solid electrolyte layers 31 and 34 and the spacer 32. The measurement gas enters the measurement gas chamber 320 through a hole 310 extending through the solid electrolyte layer 31 and a porous layer 33. The porous layer 33 is interposed between the solid electrolyte layers 31 and 34 and works as a diffusion resistor. The gas sensor element 3 also has a reference gas chamber 350 surrounded by the solid electrolyte layer 34, the spacer 35, and the insulating layer 36.

The gas sensor element 3 also includes a first electrochemical cell 41 and a second electrochemical cell 42. The first electrochemical cell 41 is made up of the solid electrolyte layer 31 and a pair of electrodes 411 and 412 affixed to the solid electrolyte layer 31. The electrode 411 is exposed directly to the measurement gas existing outside the gas sensor element 3. The electrode 412 is exposed to the measurement gas chamber 320. The electrodes 411 and 412 are of an annular shape.

The second electrochemical cell 42 is made up of the solid electrolyte layer 34 and a pair of electrodes 421 and 422 affixed to the solid electrolyte layer 34. The electrode 421 is exposed to the measurement gas chamber 320. The electrode 422 is exposed to the reference gas chamber 350. The electrode 421 is of an annular shape.

The first electrochemical cell 41 works as a pump cell which pumps oxygen ($O_2$) out of or into the measurement gas chamber 320 to or from outside the gas sensor element 3, thereby causing a flow of oxygen ion current I to be produced between the electrodes 411 and 412. The second electrochemical cell 42 works as a sensor cell which produces between the electrodes 421 and 422, an electromotive force V as a function of a difference in concentration of oxygen between the measurement gas chamber 320 and the reference gas chamber 350. The electromotive force V is used to control the voltage applied across the electrodes 411 and 412 of the first electrochemical cell 41 to keep the concentration of oxygen within the measurement gas chamber 320 constant. Specifically, the oxygen ion current I that is a function of an air-fuel ratio is developed by adjusting the oxygen ion current I to keep the electromotive force V constant so that the concentration of oxygen within the measurement gas chamber 320 may be kept constant.

The volume Vc of the measurement gas chamber 320 is, like the first embodiment, 0.15 $mm^3$ or less, thereby producing substantially the same beneficial effects as in the first embodiment.

The gas sensor element 3 is, like the first embodiment, designed to have the Vc-Sp ratio smaller than 0.02 mm (i.e., Vc/Sp<0.02 mm), thereby minimizing an error of an output of the gas sensor element 3 during transition of activation thereof. Note that Sp is an area of the electrode 412.

Figure 13:
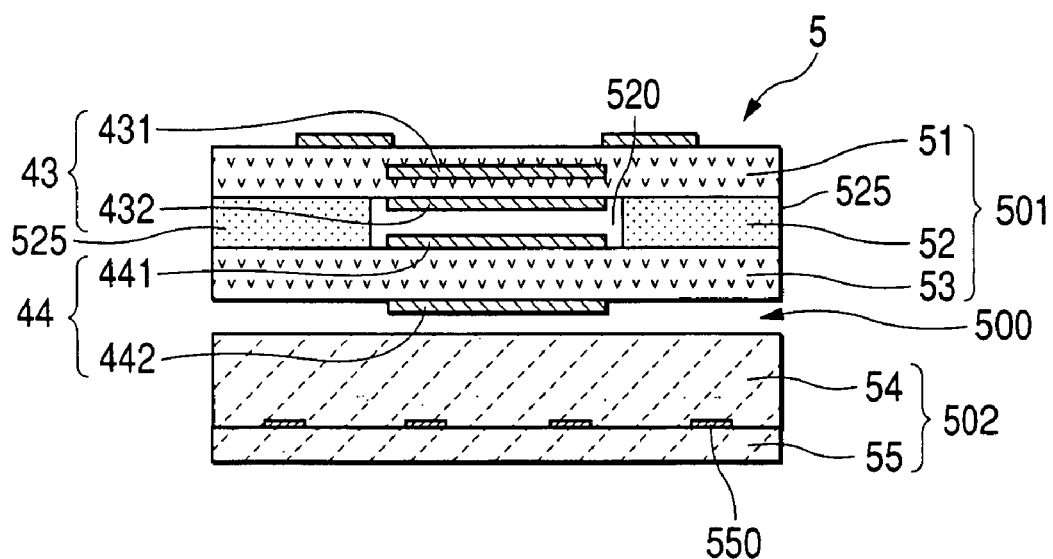
FIG. 13 is a transverse sectional view which shows a gas sensor element according to the third embodiment of the invention.
Figure 14:
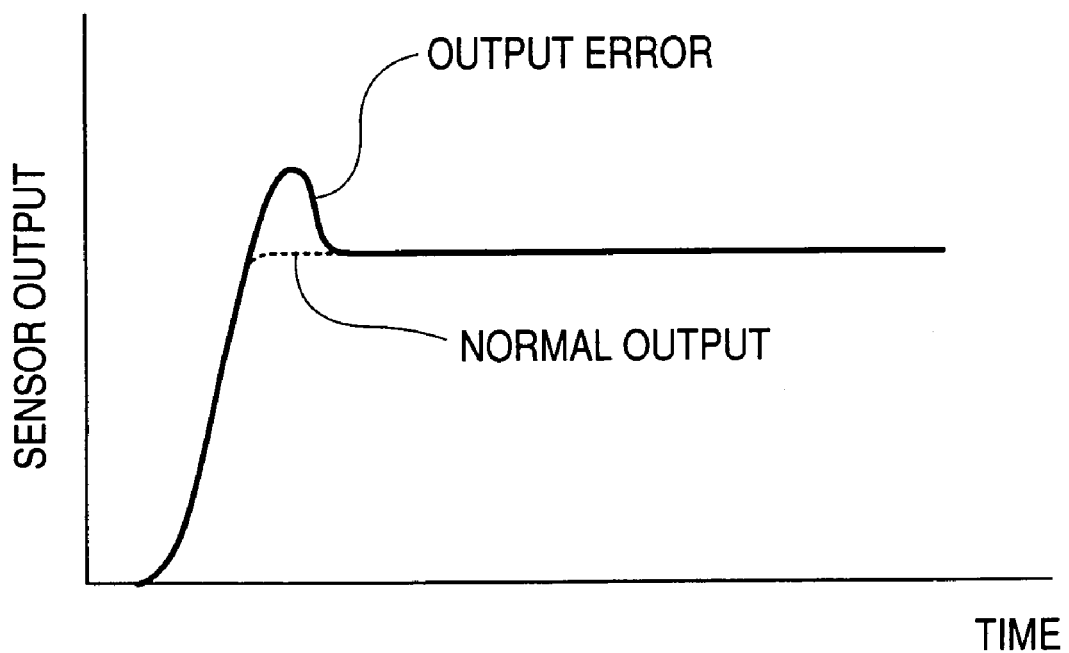
FIG. 14 is a graph which shows an error of an output of a conventional gas sensor element during transition of activation of the sensor element.

FIG. 13 shows a gas sensor element 5 according to the third embodiment of the invention which is of a two-cell type and has a separate heater 502.

The gas sensor element 5 consists essentially of an element body 501 and the heater 502 facing the element body 501 through a clearance 500. The element body 501 is made up of solid electrolyte layers 51 and 53 and a porous material-made spacer 52. The heater 502 is made up of an insulating layer 54 and a heater substrate 55 on which a heater element 550 is fabricated.

The element body 501 has a measurement gas chamber 520 defined by the solid electrolyte layers 51 and 53 and the spacer 52. The element body 501 also includes a first electrochemical cell 43 and a second electrochemical cell 44. The first electrochemical cell 43 includes an electrode 431 embedded in the solid electrolyte layer 51 and an electrode 432 exposed to the measurement gas chamber 520. The second electrochemical cell 44 is made up of the solid electrolyte layer 53 and a pair of electrodes 441 and 442 affixed to the solid electrolyte layer 53. The electrode 441 is exposed to the measurement gas chamber 520. The electrode 442 is exposed directly to the measurement gas flowing through the clearance 500 outside the gas sensor element 5.

The spacer 52 is made of a porous material and works as a diffusion resistance layer. The spacer 52 has a side surface 525 from which the measurement gas enters the measurement gas chamber 520.

The second electrochemical cell 44 is responsive to application of voltage to work as a pumping cell which pumps oxygen ($O_2$) out of or into the measurement gas chamber 520 to or from outside the gas sensor element 5, thereby causing a flow of oxygen ion current I to be produced between the electrodes 441 and 442.

The first electrochemical cell 43 is also responsive to application of a weak voltage to ionize oxygen molecules near the electrode 432 which, in turn, move toward the electrode 431, thus resulting in a potential difference V between the electrodes 431 and 432.

The oxygen ion current I that is a function of an air-fuel ratio is developed by adjusting the oxygen ion current I to keep the potential difference V constant so that the concentration of oxygen within the measurement gas chamber 520 may be kept constant.

The volume Vc of the measurement gas chamber 520 is, like the first embodiment, 0.15 mm³ or less, thereby producing substantially the same beneficial effects as in the first embodiment.

The gas sensor element 5 is, like the first embodiment, designed to have the Vc-Sp ratio smaller than 0.02 mm (i.e., Vc/Sp<0.02 mm), thereby minimizing an error of an output of the gas sensor element 5 during transition of activation thereof. Note that Sp is an area of the electrode 441.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A laminated gas sensor element comprising:
    a diffusion resistance layer;
    a gas impermeable layer affixed to a major surface of said diffusion resistance layer;
    a measurement gas chamber into which a gas to be measured is introduced through said diffusion resistance layer;
    an oxygen ion conductive solid electrolyte member;
    a measurement gas electrode affixed to said solid electrolyte member, said measurement gas electrode being exposed to the gas within the measurement gas chamber for measuring an oxygen gas component contained in the gas;
    a reference gas electrode affixed to said solid electrolyte member, said reference gas electrode being exposed to a reference gas, working as an electrochemical cell together with said measurement gas electrode; and
    a heater which heats the gas sensor element up to a temperature required to activate the gas sensor element, said heater working to increase a temperature of the gas sensor element at a rate of 100 to 250° C./sec,
    wherein said measurement gas chamber has a volume of 0.15 mm³ or less, and
    wherein said measurement gas chamber has a height of 5 to 18 μm in a thickness-wise direction of the gas sensor element.

2. A laminated gas sensor element as set forth in claim 1, wherein said measurement gas electrode works as a pumping electrode which pumps oxygen contained in the gas into or out of said measurement gas chamber, the pumping electrode having an area Sp exposed to said measurement gas chamber which meets a condition of Vc/Sp<0.02 mm where Vc is the volume of said measurement gas chamber.

3. A laminated gas sensor element as set forth in claim 1, wherein said measurement gas chamber has a height of 10 to 15 μm in a thickness-wise direction of the gas sensor element.

* * * * *